United States Patent [19]
Ford

[11] 4,292,963
[45] Oct. 6, 1981

[54] TRAINING SPLINT FOR WRIST-GANGLION

[76] Inventor: Robert S. Ford, 701 Beach Blvd., Pascagoula, Miss. 39567

[21] Appl. No.: 60,574

[22] Filed: Jul. 25, 1979

Related U.S. Application Data

[62] Division of Ser. No. 875,940, Feb. 7, 1980, abandoned.

[51] Int. Cl.³ ............................................. A61F 5/04
[52] U.S. Cl. .............................. 128/87 R; 273/189 A
[58] Field of Search ........................ 128/77, 87 R, 88; 273/189

[56] References Cited
U.S. PATENT DOCUMENTS 3,423,095  1/1969  Cox .................................. 273/189 A
4,176,840 12/1979  Lanning .......................... 273/189 A

OTHER PUBLICATIONS

"Rollstar 700" *Bowling Magazine* Feb. 1976.

*Primary Examiner*—Robert W. Michell
*Assistant Examiner*—T. Wallen

[57] ABSTRACT

An orthopedic forearm splint intended to limit dorsiflexion of the wrist, without interfering with volarflexion and use of the hand, whereby ganglions of the wrist may be caused to regress. Applies the inventor's discovery that extreme dorsiflexion is the causative or aggravating factor in wrist ganglion. Comprises a light cantilever splint secured to the dorsum of the arm by one bracelet, with the distal end elongated beyond the bracelet in cantilever fashion past the wrist and freely apposing the hand, whereby it will strike the back of the hand if dorsiflexion is attempted, but does not interfere with volarflexion or normal work. Reversible to dodge ganglions and prevent chafing.

3 Claims, 3 Drawing Figures

TRAINING SPLINT FOR WRIST-GANGLION

This application is a division of Ser. No. 875,940, filed Feb. 7, 1980, now abandoned.

BACKGROUND OF THE INVENTION

I discovered by experimenting with my own wrist-ganglion that ganglions are caused and aggravated by extreme dorsiflexion of the wrist, and that if dorsiflexion is limited without immobilizing the wrist, the ganglions will regress and disappear in a few weeks. My discovery indicates that immobilization of the joint with a cast or full arm-and-hand splint is adverse to regression of ganglions. As long as dorsiflexion is limited, other wrist movements such as volarflexion, lateral flexing, and rotation seem to help ganglions regress, by massaging them and putting them under momentary repetitive pressure. These motions tend to literally pump out the the fluid, break up the capsules, and cause them to be worn away and resorbed. Daily soaking in hot water with the wrist volarflexed is believed to speed up the resorptive action by increasing the phagocytic activity.

I invented the splint, made a series of gradually improved test samples, and wore the two-bracelet basic model about a month to obtain a permanent cure of my own ganglion.

It has previously been known in the medical arts that the fluid-filled sacs called ganglions often appear from previously unknown causes and sometimes fade away likewise. Also that they appear as immediate results of injuries such as falls on the palm of the hand, or unusually heavy strains on the wrist. Some of these injury cases have been successfully treated by conventional immobilizing casts or splints like the Futura glove-splint, but apparently there has been no previous understanding of the special aggravating effects of dorsiflexion, or the benefits obtainable by avoiding dorsiflexion without immobilization. The usual treatment for chronic ganglion in the past has been by surgical excision, resulting in unsightly scars, cratering, and a high rate of recurrence, as well as great expense from hospitalization, often at federal expense. Conservative permanent cure by this new splinting treatment is therefore an improvement much needed by both the public and the government.

My discovery indicates that ganglion formation is a protective bursa-like response to trauma resulting from extreme dorsiflexure, such as leaning heavily on the palm of the hand. When the joints are thus flexed beyond their normal angular range, the joint margins over-run one another and are traumatized, causing hypertrophy of normal structures, fluid accumulation, and ganglion formation. Apparently man shares a weakness or limitation in this regard with the other higher primates, the gorilla, chimpanzee, and orangutan, which walk and rest on their knuckles with the wrist held straight. They ordinarily do not let the heel of the hand rest on the ground like a baboon. To cure ganglions spontaneously and avoid recurrence, the human being must be taught what the apes already know: Not to lean on the retracted palm. Together with suitable explanation, my splint trains these automatic protective reflexes into the patients' mind, so for this reason I call it a training splint.

Wrists are abused in dorsiflexion in many ways, viz: Leaning heavily on the palm while brushing teeth, washing out a bathtub or vat, sawing boards, doing pushups, in bed, bracing while sitting on a bench, or in a car, etc. Not everyone lets the wrist go all the way back when doing such things, but some do, and thus ganglions are triggered. Once this happens, extreme dorsiflexion must be avoided to cause regression to occur, and the bad habit must be broken, otherwise the ganglion may recur.

BRIEF SUMMARY OF THE INVENTION

The central object of my invention therefore is to provide an orthopedic forearm device to limit dorsiflexion of the wrist, yet freely permit all other natural wrist movements and otherwise normal use of the hand, whereby ganglions will be caused to regress, and reflexes against dorsiflexion will be instilled and trained into the mind, so that ganglion recurrence will be avoided in the future.

The basic concept comprises a thin spatulate splint lashed to the forearm with the distal end projecting as a cantilever extension freely out past the wrist, apposing the back of the hand, providing a limitation to dorsiflexure by pressing against the back of the hand when the wrist begins to dorsiflex. The free cantilever portion of the splint, apposing the dorsum of the hand but not attached to it, is a distinguishing feature of the invention.

Both a basic elementary form and a greatly improved form for production are disclosed.

Ancillary objects to assist in carrying out the primary purpose in a safe, comfortable, and economic manner are as follows:

1. To avoid trauma or breakage of the device upon forcible dorsiflexion as in a fall or emergency situation, by providing elasticity in either or both the lashing or the splint, whereby the device will safely yield and spring back when overstressed, without breaking or applying traumatic forces.

2. To avoid bruising or abrading the skin, by rounding and smoothing the active point of the splint.

3. To avoid impingement of the splint directly upon the ganglion, wherever it may lie, and yet to fit either right or left arm. Ganglions are often sensitive and sore, as well as easily abraded due to their prominence, so will not stand direct action of the splint. Since ganglions occur in various spots across the dorsum of the wrist in different cases, though usually toward the inward margin, it was a problem to create a splint which is fully reversible by the user to both dodge ganglions, fit either arm, yet not project laterally enough to catch in the coat-sleeve.

4. To obtain stability of the splint, so it will remain in the desired location on the arm, without skewing or working around to the lateral or ventral aspect of the arm.

5. To avoid absorption of water, perspiration, and soiling so that the device can be worn continuously night and day, even in the bath or lavatory, without necessity to remove it for washing and drying.

6. To provide ventilation of the large splint area lying upon the skin, whereby perspiration may evaporate, and growth of fungus be prevented.

7. To minimize discomfort and interference with normal working use of the hand, so the wearer will not suffer inconvenience or lost time from work.

8. To provide for a smart and stylish appearance, to minimize questions and embarrassment to the wearer.

9. To minimize overall size and production costs, whereby the devices can be manufactured in quantity for sale at reasonable prices.

DETAILED DESCRIPTION

Figure 1:
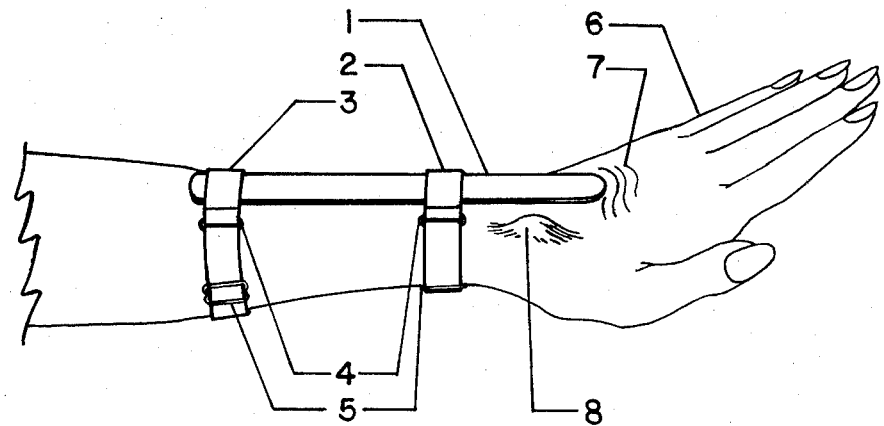
FIG. 1 is a view of the basic two-bracelet splint on a left wrist with typical large ganglion, looking from the right side downward. The wrist is shown slightly dorsiflexed to the maximum permitted by the splint, which is shown apposing the back of the hand, slightly indented into and wrinkling the skin.
Figure 2:
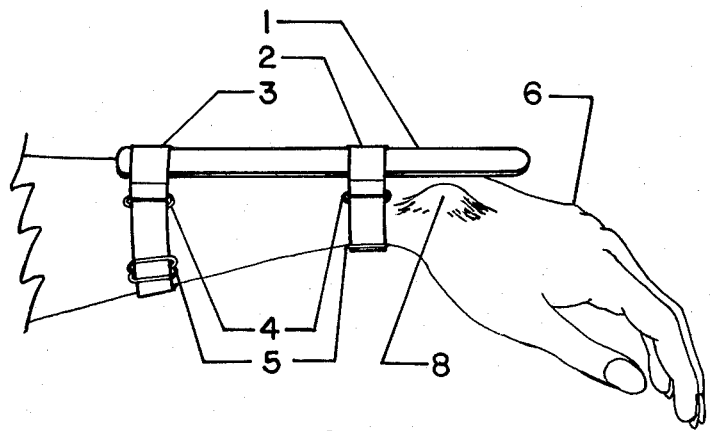
FIG. 2 is a similar view with the wrist slightly volarflexed in a normal resting position. The hand is completely free from the splint, at ease, and ready to do useful work. The ganglion is drawn larger in this view, for ganglions peak up momentarily during volarflexion due to pressures generated deep in the wrist. It appears in this view that the splint 8 is about to bear down on the ganglion, which is not intended, as it might be painful and harmful. This possibility shows the disadvantage of a laterally symmetrical splint, which may in some cases bear against the ganglion.

FIGS. 1 and 2 show the most basic form, comprising a straight spatula-shaped substantially stiff or springy splint 1, adapted to be lashed to the forearm with bracelets 2 and 3. Splint 1 projects distally beyond the distal bracelet 2 as a free cantilever section, over the wrist and out over the hand, freely apposing the back of the hand when the hand is in a substantially straight position relative to the arm, but not to be attached to the hand. In use, this cantilever section of the splint is the functional member, substantially preventing dorsiflexion and reminding the wearer not to dorsiflex, by means of the tip end of splint 1 forcibly apposing and digging into the back of the hand when dorsiflexion is attempted, yet not attached to the hand or interfering with volarflexion and normal use of the hand.

In this form, the splint 1 is a flattened spatula with wellrounded ends and edges, made of wood or springy plastic such as nylon, about 18 cm long by 2 cm wide by 2 to 3 mm thick, projecting beyond the distal bracelet about 6 cm. The bracelets 2 and 3 are made of elastic webbing about 2 cm wide, so they can instantly be stretched on or off over the hand. Conventional slides 5 and links 4 provide for bracelet adjustment to fit any arm. These elastic bracelets are sewed with loops to retain the splint 1, and are glued thereto.

For purposes of analyzing the inventive concept and scope of this disclosure, the splint 1 as shown in FIGS. 1 & 2 may be mentally divided into two portions, viz: The portion between the bracelets 2 and 3 is the "foundation shank", or "footing lever", and the portion shown projecting out over the hand is the "cantilever splint", which is the essential active member serving to appose the dorsiflexed hand. As long as the tip of the cantilever splint is maintained in the described space relationship with the arm and hand, the concept and teaching of the invention will be put to practice. Even if the cantilever splint were arched up over the wrist in gooseneck fashion, or in any other peculiar shape, the inventive concept is still carried out if the tip freely apposes the back of the straightened hand as described. The foundation shank could be a saddle, a cast, cuff or any other form capable of supporting the cantilever splint in the described space relationship, without departing from the inventive concept disclosed.

The means for fastening the foundation shank to the forearm is herein referred to as the lashing, even if it were metal bracelets or a plaster cast, to use basic terminology originated in early times when splints were mere wooden sticks lashed to the limb with a cord or thong. The lashing could be almost anything that would encircle the arm, for instance cloth, metal bracelets, rubber, elastic webbing, leather, plastic, or even a plaster cast or full gauntlet cuff. Any of a wide range of latches, catches, seals, clips, staples, laces, ties, Velcro fasteners, elastics, buckles, etc. could be used for securing and releasing the lashing, without departing from the inventive concept disclosed.

The dimensions given are convenient for the normal adult, but are not critical, and could evidently be varied over a wide range without departing from the concept and function of the invention. Likewise, it is evident that a wide range of materials and details of construction would be effective. The cantilever splint 1 and its foundation shank could be made in different pieces and of any stiffish materials, for instance wood, metal, plastic, gypsum plaster, etc., and need not be straight.

When breakable or stiff materials such as wood, heavy metal, plaster, etc. are used for the splint member, the lashing should be elastic to permit yielding and thus prevent breakage or injury in case of strenuous dorsiflexion or accident. If yielding springy materials such as thin plastic splints are used, the lashing can be non-elastic, such as nylon webbing, etc.

For application by a doctor to persons of inadequate motivation or competence, bracelets should be used which cannot be removed unless they are cut loose. Such bracelets may be made of non-elastic material, fastened with non-releasing clasps, staples, or rivets.

Figure 3:
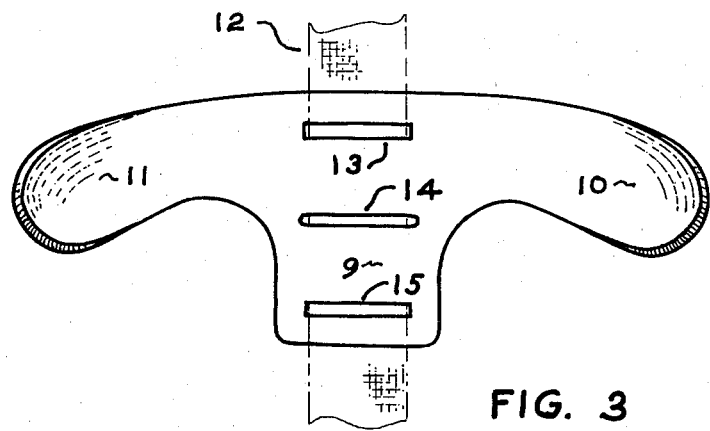
FIG. 3 is a plan view of the improved reversible single-bracelet splint, shown with a section of web bracelet strap rigged through the securing slots. The views of the patient's hand and arm with ganglion in FIGS. 1 and 2 may be utilized to study the application of this single-bracelet splint. This improved splint is applied to the dorsum of the arm with the bracelet at the point in FIGS. 1 and 2 occupied by bracelet 2. In this position, the ganglion lies clear of the splint arm, within the area embraced by the curved offset arm 10, and the convex lower side of the spooned tip of arm 10 lies upon the dorsum of the hand, limiting dorsiflexion without impinging on the ganglion.

FIG. 3 shows a highly improved reversible single-bracelet splint, which has many advantages. It is made of hard springy plastic like nylon, approximately 1.5 to 2 mm thick, by 12 to 14 cm long, by either die cutting and forming sheet material, or by high speed injection molding.

Referring to FIG. 3, although in practice the splint is best made in one piece, for purposes of description the various portions of it are given separate reference numbers. Viewing the splint as if it were being worn on a left hand with right ganglion as in FIG. 2, the bracelet 12 would be located on the distal end of the forearm next to the wrist joint, at the position occupied by the distal bracelet 2 in FIG. 2. The bracelet 12 is a woven fabric or flexible PVC strap about 18 mm wide, with buckle or clasp, rigged as shown through slots 13 and 15 in the central plate 9 near its lateral margins. Slot 14 is a perforation for ventilation, avoiding fungus growth from perspired moisture. This perforation could be any shape or size, perhaps a decorative pattern or group of small openings.

The plate 9 serves as a central base or shank supporting the cantilever splint arms 10 and 11 extending therefrom. Plate 9 is maximally widened as much as the width of a forearm permits, for increased stability as later described.

The entire splint may be optionally reversed end for end to avoid direct harmful impingement on a ganglion wherever it may be on the wrist of either arm. This versatility and ganglion dodging function is attained by the opposite laterally offset positions of the two arms 10 and 11 with respect to plate 9. As shown in FIG. 3, these arms are attached at the lateral edge of plate 9 instead of at its center, thus being offset away from the center of plate 9 as far as possible. When these arms 10 & 11 are individually viewed from the center of the plate 9, it is evident that arm 10 is on the viewer's left, and arm 11 is on the viewer's right, showing in effect that the direction of the offset in the mounting position of arms 10 and 11 is opposite or reversed from one another, even though they both lie along the same longitudinal lines of the appliance per se. By virtue of this feature, if the wearer finds one of the splint arms 10 or 11 hurting his ganglion, he need only turn the whole appliance end for end, whereupon the other splint arm comes into play on the opposite side of his wrist free and clear. Or if incidental chafing occurs, relief can be obtained by reversal. Even if the wearer has ganglions on both wrists, this advantage still applies with full effect, no matter where the ganglions are located. Although I have described the act of splint reversal as "end for end" for clarity, it is important to understand that such a reversal inherently entails also a "side for side" reversal, which in my invention switches the active splint arm from one side of the wrist to the other.

In a position on the wrist as described above, arm 10 is the active cantilever splint arm apposing the back of the hand to limit dorsiflexion, whilst arm 11 lies upon the forearm acting as a footing lever preventing proximal tilting of the plate 9 by the moments generated from hand pressure upon the tip of arm 10. When the splint is reversed to dodge a left margin ganglion, of course arm 11 becomes the active cantilever arm, and arm 10 becomes the footing lever.

If the offset arms 10 and 11 were straight as in previous splints, the active tips thereof would appose the hand and arm near the lateral margins thereof, where they would be prone to catch in the clothing and be generally impractical. To eliminate this liability, I have inwardly re-curved the arms 9 & 10 back toward the center of the plate 9, so that the active tips of arms 10 and 11 land more nearly on the center of the hand and arm, still retaining the capability of dodging ganglions on the wrist as earlier described.

The tips of both arms 10 and 11 are smoothly dished upward or "spooned" like the bowl of a spoon or rounded like a knob to avoid trauma of the skin, both constructions being referred to in the term "spooned". As earlier described herein with reference to FIG. 1 and FIG. 2, this FIG. 3 splint can be made with plain well-rounded flat tips instead of spooned tips, and likewise can be made of several separate pieces fastened together instead of all in piece, without departing from the utility and scope of the invention.

This single-bracelet splint can be more easily described in its finished form by comparing it to the capital letter T as it is normally written on a flat surface. The central base plate 9 is like the stem of the T, and in use is secured across the distal end of the forearm by a bracelet strap rigged through slots 13 and 15 in the plate, or by other equivalent lashing means secured to the plate. The two opposing splint arms 10 and 11 may be considered as one curved and drooping arcuate member extending across and containing the upper end of the T stem, which is actually the center base plate 9, thus forming the top of the letter T and completing the likeness of a somewhat stumpy letter T with rounded and curving arms drooping toward the base of the T stem.

This FIG. 3 single-bracelet splint has greatly improved stability, minimizing the tendency to move sidewise or skew on the wrist. Stability is the object of widening the center plate section 9, which operates as follows: If the edge of plate 9 approaches the side of the wrist, the bracelet then pulls on the plate along an almost transverse line, decreasing any tendency to pull the plate further aside. Simultaneously, the bracelet tension is increased, and it pulls on the opposite side of plate 9 along a more parallel line, thus tending to pull the plate back toward center. Likewise, if the plate starts to skew around at an angle to the arm, the maximally widened space between the attachment slots 13 and 15 permits rapid development of a force-couple lever arm by which the increasing tension in the bracelet exerts a powerful righting torque which tends to return the plate to its normal straight position. The wide bracelet strap uses a similar force-couple principle to promote stability, so that when skewing begins, the strap goes slack on opposite edges, developing a restoring forcecouple lever arm between the two lines of tension along the opposite band edges.

Thus by virtue of the widened plate section, (as wide as the wrist permits, 40 to 60 mm) and the side strap, which could profitably be made as wide as 25 or 30 mm, the FIG. 3 style is far more stable with only one bracelet than the FIGS. 1 and 2 style is with two, as well as smaller, more stylish, more comfortable to wear, and cheaper to produce.

With a web nylon or plastic strap and a plastic splint, the reversible FIG. 3 splint absorbs very little water, so it can be worn in the bath, and can easily be wiped clean and dry on the arm without removal. This is important, because many people damage their wrists in their bathroom habits. A noncorroding stainless steel buckle is normally provided. A non-releasing snap-clip is provided for use by doctors on incompetent or inadequately motivated patients.

As above described in detail, this application discloses an inventive range of remarkably broad scope, beginning with an original biological discovery, extending through all the stages of discovering a need for a remedial appliance, conceiving an appliance containing certain functionl means, creating the basic elementary form, and advancing to a highly perfected consumer product suitable for automatic machine production.

I claim:

1. In an orthopedic appliance adapted for attachment to the distal end of the forearm by lashing means embracing the said forearm adjacent to the wrist, an appliance having a shape analogous to the letter "T", combining a central base plate comparable to the stem of a T to be secured across the distal end of the forearm by lashing means including lashing attachment means provided on the said plate, an arcuate double-ended splint member comparable to the combined upper arms of a letter T extending across and containing the upper end of the said central base plate comparable to the T stem, the said arcuate member being formed in a curving shape with the tips drooping toward the base of the letter T, whereby one tip of the said arcuate splint arm will appose the dorsum of the hand to prevent dorsiflexion without contacting a wrist-ganglion, while the opposite tip will serve as a footing lever against the forearm, the whole device being reversible at will to obtain optional or right positions of the active splint arm upon either wrist, so as to permit dodging ganglions wherever they may lie.

2. An appliance as in claim 1 wherein the tips of the said arcuate double-ended splint member are spooned.

3. An appliance as in claim 1 wherein the tips of the said arcuate double-ended splint member are plain well-rounded flat tips.

* * * * *